United States Patent
Kumar et al.

(10) Patent No.: US 12,295,476 B2
(45) Date of Patent: May 13, 2025

(54) SKIN PREPARATION DEVICE FOR CLEANING CATHETER LINE AND HUB

(71) Applicant: Becton, Dickinson and Company, Franklin Lakes, NJ (US)

(72) Inventors: Manish Kumar, Bengaluru (IN); Karthik Mr, Bangalore (IN); Shishir Prasad, Ramsey, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 17/982,083

(22) Filed: Nov. 7, 2022

(65) Prior Publication Data

US 2024/0148126 A1 May 9, 2024

(51) Int. Cl.
| | |
|---|---|
| *B43K 5/14* | (2006.01) |
| *A45D 34/04* | (2006.01) |
| *A61M 35/00* | (2006.01) |

(52) U.S. Cl.
CPC ........... *A45D 34/04* (2013.01); *A61M 35/003* (2013.01); *A61M 35/006* (2013.01)

(58) Field of Classification Search
CPC .......................... A61M 35/003; A61M 35/006
USPC .................................................... 401/132
See application file for complete search history.

(56) References Cited

U.S. PATENT DOCUMENTS

| | | | |
|---|---|---|---|
| 6,729,786 B1 | 5/2004 | Tufts et al. | |
| 6,991,394 B2 | 1/2006 | Tufts et al. | |
| 7,182,536 B2 | 2/2007 | Tufts et al. | |
| 7,241,065 B2 | 6/2007 | Tufts et al. | |
| 7,422,388 B2 | 9/2008 | Tufts et al. | |
| 7,824,122 B2 | 11/2010 | Flores et al. | |
| 7,993,066 B2 | 8/2011 | Flores et al. | |
| 8,348,913 B2 * | 1/2013 | Hoang .................. | A45D 34/04 604/3 |
| 8,702,751 B2 * | 4/2014 | Stenton ............... | A61M 35/003 606/214 |
| 8,740,488 B2 * | 6/2014 | Cable .................. | A61M 35/003 401/133 |
| 11,027,032 B2 | 6/2021 | Degala et al. | |
| 11,647,984 B2 * | 5/2023 | Arant ................. | A45D 40/0087 600/459 |
| 2002/0076255 A1 | 6/2002 | Hoang et al. | |

OTHER PUBLICATIONS

International Search Report and Written Opinion corresponding to PCTUS23078769; mailed Dec. 18, 2023, (9 pages).
Carefusion Corporation, "ChloraPrep® 26mL Applicator", Application instruction sheet, 2011, (1 page).

* cited by examiner

*Primary Examiner* — Jennifer C Chiang
(74) *Attorney, Agent, or Firm* — Myers Bigel, P.A.

(57) ABSTRACT

A skin preparation device including a body member, a fluid retention member operatively connected to a distal end of the body member, and a tip extending radially from an outer surface of the fluid retention member.

20 Claims, 6 Drawing Sheets

FORCE EXERTED BY HUB

SKIN PREPARATION DEVICE FOR CLEANING CATHETER LINE AND HUB

BACKGROUND OF THE INVENTION

Field of the Invention

The present disclosure relates generally to a device for cleaning an intravenous line and/or hub. More particularly, the present disclosure relates to a device for cleaning an underside of a catheter line or hub while reducing or eliminating a risk of dislodging the catheter line or hub from a patient.

Description of Related Art

An intravenous (IV) set is currently used to access the circulatory system of a patient, enabling the administration of fluids and medications in a controlled, predictable manner. One particular example of an IV set is a catheter line and hub inserted into the patient. Typical IV sets may include a primary fluid flow line of tubular construction with one or more access points positioned along its length. Some of these access points can comprise access ports that allow for the administration of medications through either a syringe or by infusion through another IV set. A primary access point is located at one end of the IV set with a fluid source, such as saline, contrast medium, or blood, among other types of fluid. Secondary flow lines may be combined with the primary flow line to provide additional or alternative fluids to the patient.

Use of IV sets has now become integral at every stage of medical care, from the site of an accident or injury, through transport to the hospital, during emergency room and surgical procedures, and potentially continuing into the Intensive Care Unit and general hospital care. At each stage of procedure or treatment of the patient, different medical personnel typically become involved with attending to the patient.

When multiple medical personnel are involved, the combinations of procedures involving the multiple IV sets become even more complex and can lead to greater risk of the IV line becoming dislodged from the patient's vasculature. This is particularly true with respect to surgical procedures in an operating room in which medical personnel may be attending to several different issues or problems with a patient that require the medical personnel to move about the patient. In addition to the surgical staff having to focus on specific medical problems, other personnel may be involved, such as an anesthesia provider who typically administers anesthesia medications via the IV set, all of which increase the risk of an individual inadvertently dislodging the IV set or line from the patient.

After a patient has been attended to during a surgical procedure, the IV line and/set may be kept in the patient's vasculature during recovery of the patient to provide needed nutrients and/or blood to the patient. Since the IV line and/or set may be used with the patient for an extended length of time, the IV line and/or the patient's skin surface may need to be cleaned and/or sterilized at periodic times during the patient's recovery. However, in order to clean the IV line and/or set, the IV line and/or set may need to be lifted to gain access underneath the IV line and/or set, which increases the risk that the IV line and/or set becomes inadvertently dislodged from the patient.

Therefore, in view of the foregoing problems, a need exists in the art for a device or tool that permits an individual, such as medical personnel, to clean and/or sterilize an underside of an IV line and/or set and/or a patient's skin surface without inadvertently dislodging the IV line and/or set from the patient.

SUMMARY OF THE INVENTION

In view of the foregoing, according to one non-limiting embodiment or aspect of the present disclosure, a skin preparation device may include a body member, a fluid retention member operatively connected to a distal end of the body member, and a tip extending radially from an outer surface of the fluid retention member.

In another non-limiting embodiment or aspect of the present disclosure, the body member may be tubular and define a hollow cavity to receive a disinfectant within the hollow cavity. The fluid retention member may include a sponge or foam. A base member may be formed on the distal end of the body member, in which the fluid retention member may be operatively connected to the base member. At least one activation member may extend radially from the body member, in which the at least one activation member may be configured to release disinfectant held in the body member to the fluid retention member. The tip may define a slot or channel. An angle established between the slot or channel and a horizontal surface on which the skin preparation device rests may be 165 degrees at a maximum. The fluid retention member may be replaceable on the body member. The tip may be tapered from an upper surface to a bottom surface. The tip may taper at a maximum angle of 15 degrees relative to a horizontal surface on which the fluid retention member rests. A diameter of the tip may be less than a diameter of the fluid retention member. An angle that defines the tip extending from the fluid retention member may be a minimum of 115 degrees.

In another non-limiting embodiment or aspect of the present disclosure, a skin preparation device may include a body member, a fluid retention member operatively connected to a distal end of the body member, and a tip extending radially from an outer surface of the fluid retention member, in which the tip is operatively connected to the fluid retention member by a living hinge.

In another non-limiting embodiment or aspect of the present disclosure, a cut-out may be defined between the tip and the fluid retention member. The tip may be configured to move about the living hinge towards the fluid retention member upon a force being applied to an upper surface of the tip. The fluid retention member and the tip may be made of a sponge or foam. The tip may define a slot or channel. An outer diameter of the tip may be less than an outer diameter of the fluid retention member.

In another non-limiting embodiment or aspect of the present disclosure, a method of cleaning or disinfecting a catheter hub or catheter line may include positioning a fluid retention member of a skin preparation device against a skin surface of a patient, in which the fluid retention member may include a tip defining a slot or channel, and moving the fluid retention member in a sideways rotational movement about the catheter hub or catheter line. The tip of the fluid retention member may be configured to deflect upon a force being applied to an upper surface of the tip.

DESCRIPTION OF THE INVENTION

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

The present disclosure is directed to a device for cleaning a catheter line and/or a catheter hub inserted into a patient. In particular, the present disclosure is directed to a device that improves medical personnel's ability to clean an underside of a catheter line and/or catheter hub without dislodging the catheter line and/or catheter hub from the patient.

Figures 1, 2:
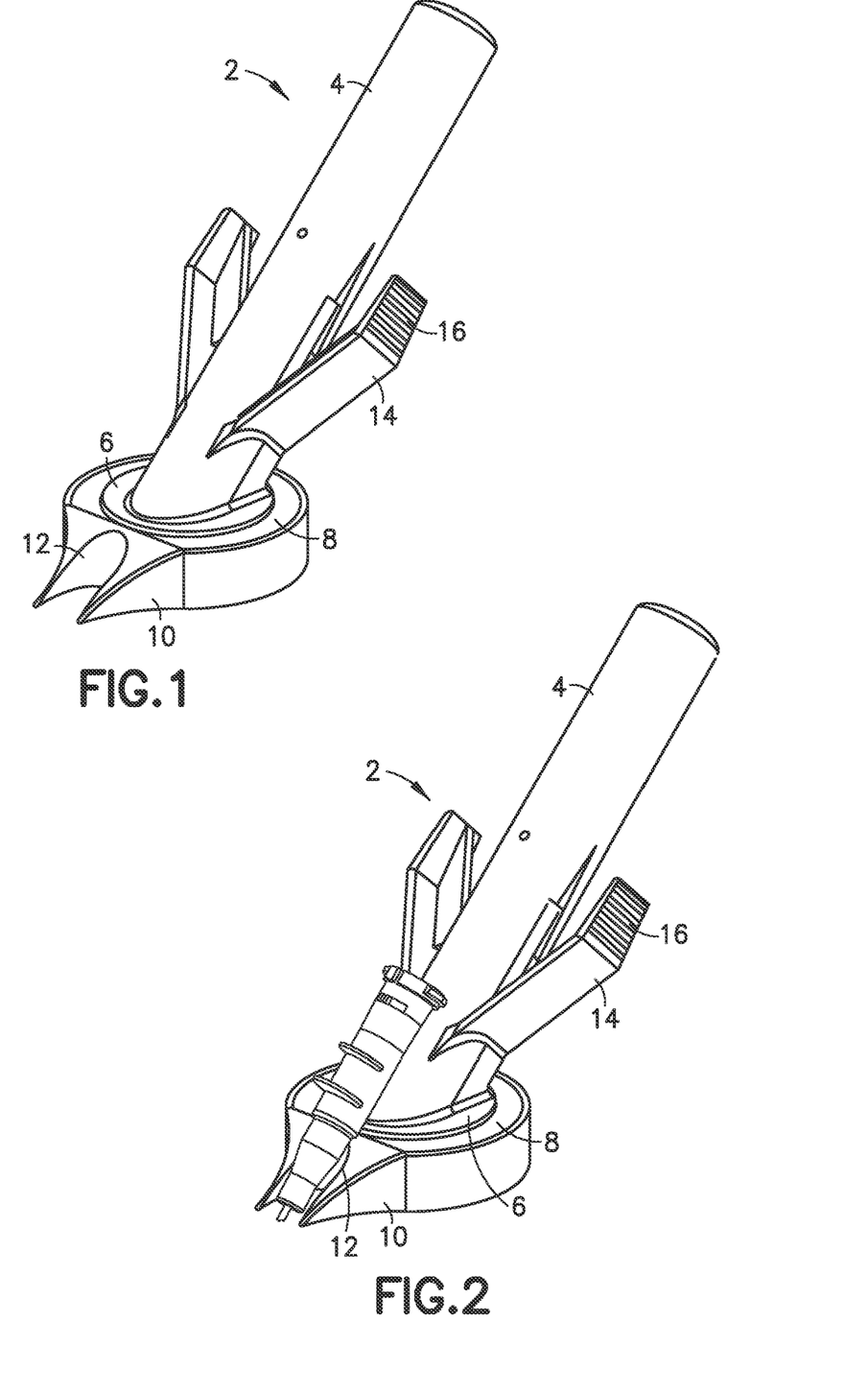
FIG. 1 is a perspective view of a skin preparation device according to one non-limiting embodiment or aspect of the present disclosure.
FIG. 2 is a perspective view of the skin preparation device of FIG. 1 used with a catheter hub.

With reference to FIG. 1, according to one non-limiting embodiment or aspect of the present disclosure, a skin preparation device 2 for cleaning and/or sterilizing a patient's skin surface and/or an IV line or set is illustrated and described in detail. The skin preparation device 2 may include a tubular body member 4 and a base member 6. The base member 6 may be positioned on a distal end of the tubular body member 4. It is also to be understood that the tubular body member 4 may have any type of cross-sectional design. In one example, the tubular body member 4 may have a cylindrical shape. In one example, the tubular body member 4 may be hollow and define an inner cavity configured to hold and seal a disinfectant within the hollow cavity. The disinfectant may be poured directly into the hollow cavity or may be held in a cartridge that is slid into the hollow cavity. It is also contemplated that the tubular body member 4 may be refilled with disinfectant after the tubular body member 4 has been emptied. It is also to be understood that fluids other than disinfectant could also be poured or delivered into the cavity of the tubular body member 4. In one example, the base member 6 extends radially outward from the distal end of the tubular body member 4. The base member 6 may have a diameter greater than a diameter of the tubular body member 4. It is also contemplated that the base member 6 is not provided with the tubular body member 4 or has the same diameter as the tubular body member 4.

With continued reference to FIG. 1, according to one non-limiting embodiment or aspect of the present disclosure, a fluid retention member 8 may be positioned on a distal end of the base member 6. In one example, the fluid retention member 8 may be a sponge or foam. The fluid retention member 8 may be formed integral with the base member 6 or may be attached to the base member 6 using an adhesive, welding, or any other attachment means. The fluid retention member 8 may be used to hold and release the disinfectant held in the tubular body member 4 onto a patient's skin surface and/or a catheter line and/or hub. The disinfectant held in the tubular body member 4 may be directed from the tubular body member 4 to the fluid retention member 8 for application on the patient's skin surface and/or the catheter line and/or hub. In the example of a sponge, the disinfectant is held in the open cell structure of the sponge for release onto the site to be cleaned. In one example, the fluid retention member 8 may be circular in shape, but alternative shapes for the fluid retention member 8 are to be considered. It is also contemplated that, after a number of uses or after a single use, the fluid retention member 8 can be removed from the base member 6 and replaced with a new, clean fluid retention member 8. It is also contemplated that the fluid retention member 8 may be made of woven or non-woven fabric, knitted fabric, or a thermoplastic elastomer.

Figure 3:
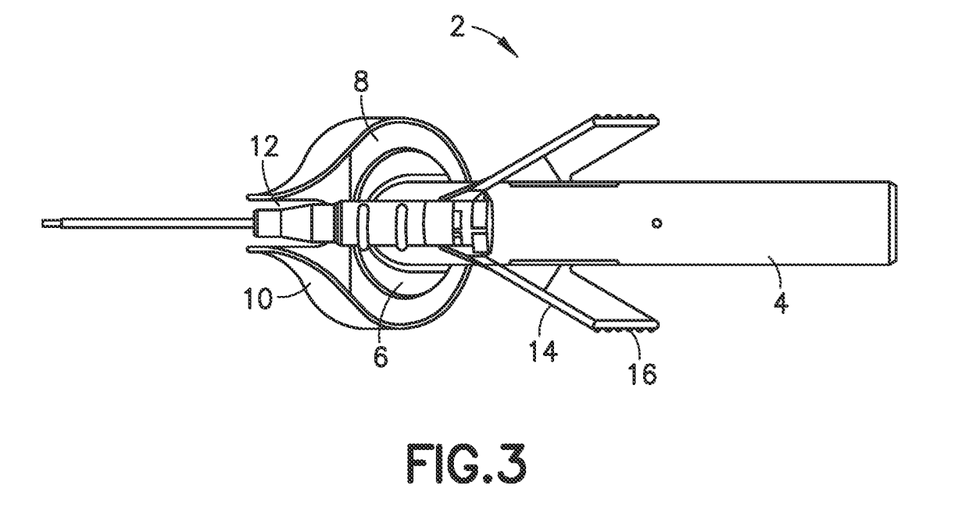
FIG. 3 is a top view of the skin preparation device of FIG. 1 used with the catheter hub.

With reference to FIGS. 1-3, according to one non-limiting embodiment or aspect of the present disclosure, the fluid retention member 8 may include a tip 10 that extends radially from the body of the fluid retention member 8. The tip 10 may be a protrusion extending from the fluid retention member 8 body. In one example, the tip 10 may define a slot or channel 12. The slot or channel 12 may extend radially relative to the distal ends of the tubular body member 4 and the base member 6. The tip 10 may be configured as an extension of the fluid retention member 8 and may be shaped so as to easily clean the underside of a catheter hub and site of insertion on a patient's skin surface without the need for inverting the tip of the skin preparation device 2, which is done with the current skin preparation devices that causes dislodging of the catheter line and/or hub from the patient. The tip 10 of the fluid retention member 8 may be used to slide underneath the catheter hub without contacting the catheter line. The tip 10 may also be used to clean the site of insertion around the catheter hub. In one example, the slot or channel 12 may be configured to hold and house the catheter line and/or catheter hub for disinfection of the underside of the catheter line and/or catheter hub. A use of the skin preparation device 2 may position the tip 10 such that the slot or channel 12 receives the catheter line and/or catheter hub to permit the user to slide the skin preparation device 2 along the catheter line and/or catheter hub to allow the fluid retention member 8 to apply the disinfectant to the underside of the catheter line and/or catheter hub.

With continued reference to FIG. 1, according to one non-limiting embodiment or aspect of the present disclosure, the skin preparation device 2 may also include an activation member 14 configured to release the disinfectant from the tubular body member 4 to the fluid retention member 8 to apply the disinfectant to the catheter line and/or catheter hub and/or the patient's skin surface. In one example, the activation member 14 is configured as a pair of "wings" that extend radially and axially from the tubular body member 4. The "wings" of the activation member 14 may be squeezed towards one another, i.e., inwardly towards the tubular body member 4, to release disinfectant from the cavity of the tubular body member 4 into the fluid retention member 8. In one example, an exterior portion of the "wings" of the activation member 14 may include a gripping portion 16 that includes ridges to assist a user in gripping the activation member 14. In one example, inside the tubular body member 4 is assembled a sealed glass cartridge which is filled with disinfectant. Once the activation members 14 are pressed inwards, due to the pressure created on the glass cartridge/ampoule, the pressure of the activation members 14 breaks, thereby releasing the disinfectant into the fluid retention member 8.

Figure 4:
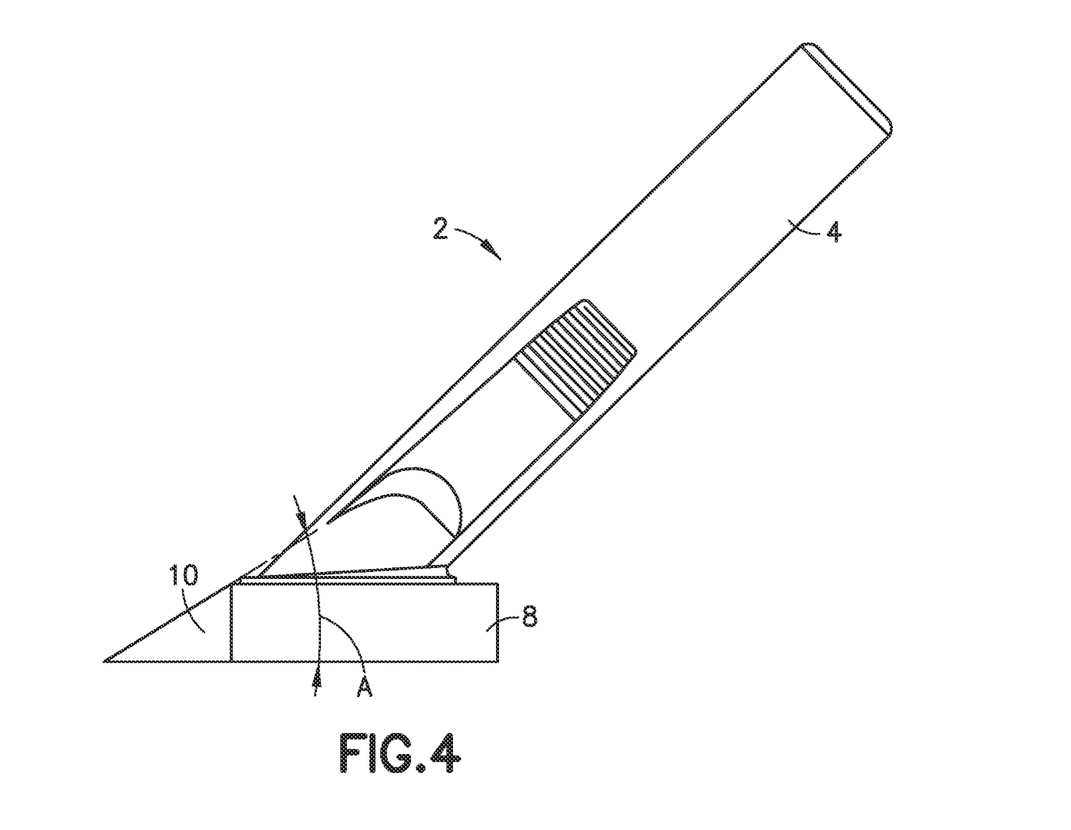
FIG. 4 is a side view of the skin preparation device of FIG. 1.

With reference to FIG. 4, according to one non-limiting embodiment or aspect of the present disclosure, the tip 10 of the fluid retention member 8 may taper down from a top surface of the fluid retention member 8 to a bottom surface of the fluid retention member 8 at an angle A. The angle A determines the extent of travel of the fluid retention member 8 underneath the catheter line and/or catheter hub/extension tube, which may be critical in accessing the site of insertion into the patient. In one example, the maximum angle for angle A may be 15 degrees. In on example, the angle A may be in the range of 0-30 degrees.

Figure 5:
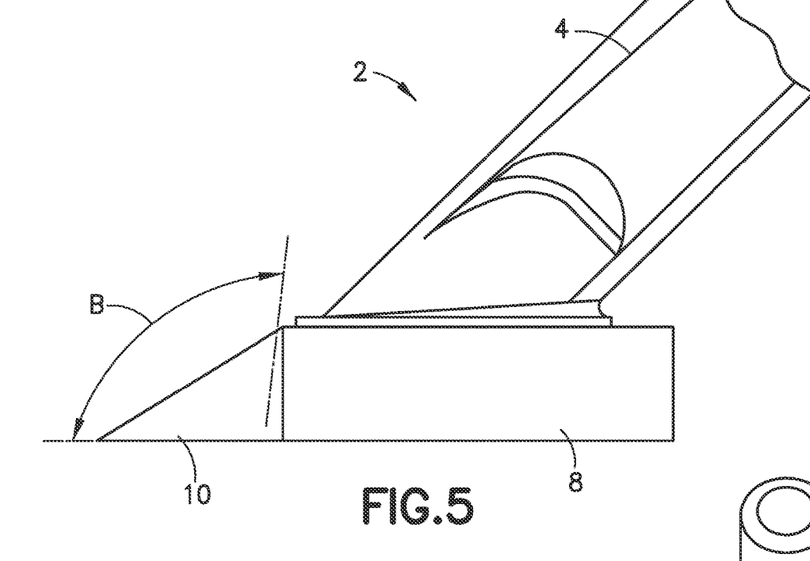
FIG. 5 is a side view of the skin preparation device of FIG. 1.

With reference to FIG. 5, according to one non-limiting embodiment or aspect of the present disclosure, the slot or channel 12 of the tip 10 may make an angle B with the horizontal surface below the skin preparation device 2. Angle B determines the coverage area of the underside of the catheter hub's external surface as the catheter hub rests on the slanted surface of the tip 10 when the site of insertion is accessed by the skin preparation device 2. In one example, angle B may be up to a maximum of 165 degrees. In one example, the angle B may be in the range of 0-175 degrees.

Figure 6:
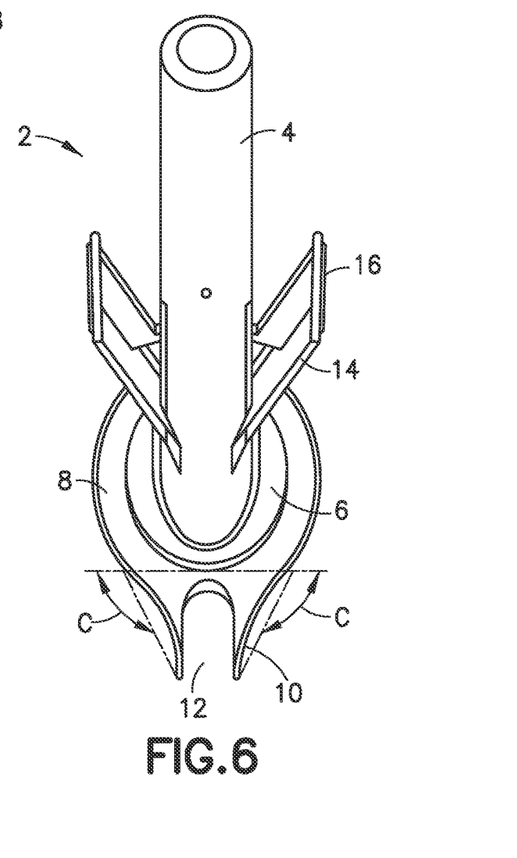
FIG. 6 is a top view of the skin preparation device of FIG. 1.

With reference to FIG. 6, according to one non-limiting embodiment or aspect of the present disclosure, a width of the tip 10 may be created based on an angle C established between the tip 10 and the outer width of the fluid retention member 8. The angle C determines the front tip width to ensure the skin preparation device 2 accommodates the largest catheter hub diameter. The angle C may be critical in holding the catheter hub within the slot or channel 12 for gripping during cleaning of the underside of the catheter hub. In one example, angle C is at a minimum of 115 degrees. In one example, the angle C may be in the range of 0-135 degrees.

Figures 7, 8:
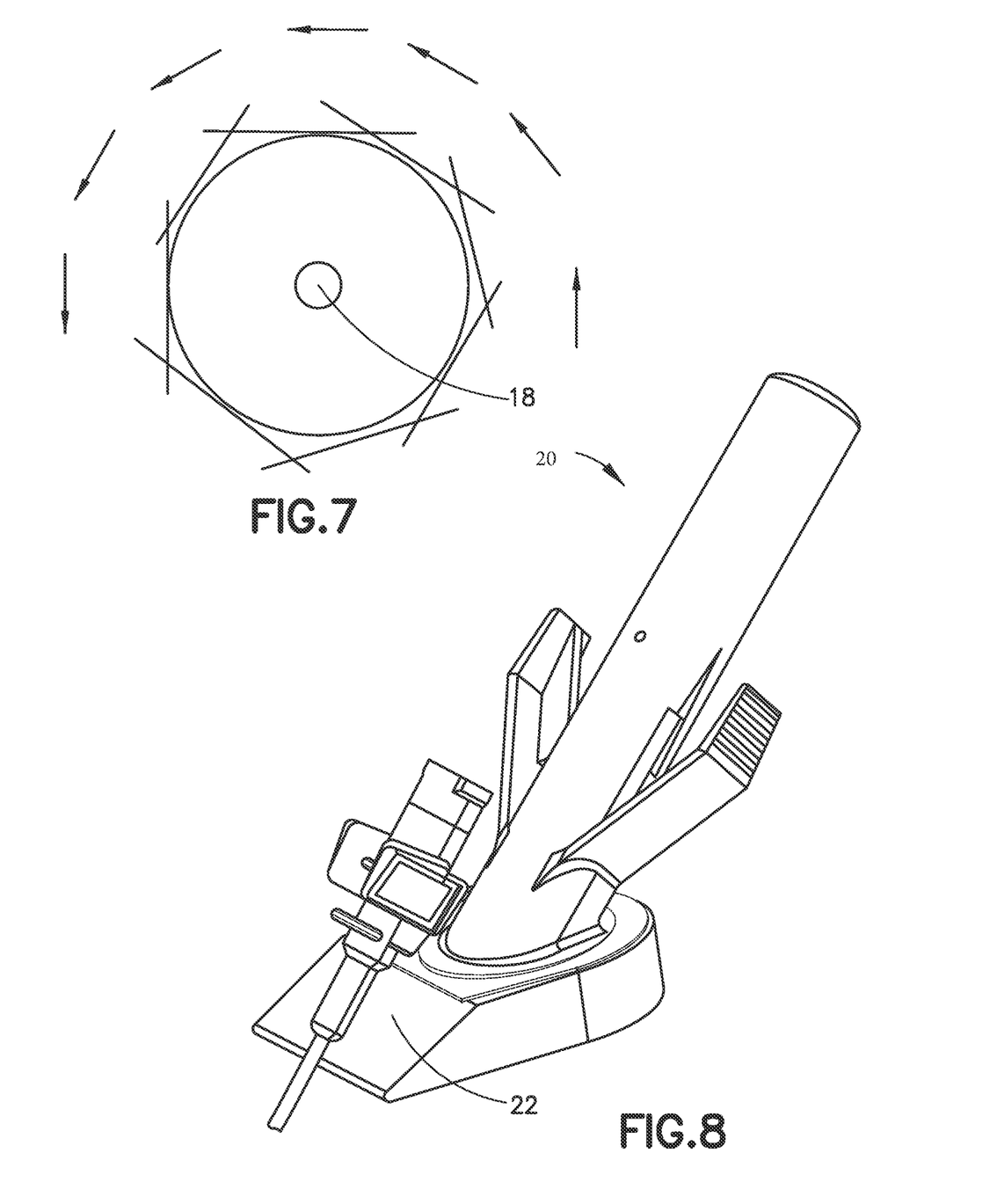
FIG. 7 is a schematic illustration of a movement of the skin preparation device of FIG. 1 about a site of insertion.
FIG. 8 is a perspective view of a skin preparation device according to another non-limiting embodiment or aspect of the present disclosure.

With reference to FIG. 7, according to one non-limiting embodiment or aspect of the present disclosure, the technical principles of using the skin preparation device 2 at a site of insertion 18 of the catheter line are shown and described in detail. The skin preparation device 2 may have a locus of sideways rotation around the catheter hub or site of insertion 18. The locus of sideways rotation cleans and disinfects the catheter hub and site of insertion 18 around the entire circumference of the site of insertion 18 without the need to invert the tip 10 of the skin preparation device 2. The locus of sideways rotation of the skin preparation device 2 reduces the effort by converting multiple transverse movements of the fluid retention member 8 to rotation of the fluid retention member 8 around the site of insertion 18, which acts as a pivot point.

With reference to FIG. 8, according to one non-limiting embodiment or aspect of the present disclosure, a skin preparation device 20 may not include the slot or channel 12 of the skin preparation device 2 described above. In particular, instead of defining a slot or channel 12 in the tip 10 of the fluid retention member 8, the tip 22 of the skin preparation device 20 may taper in a downward direction to create a thin edge of sponge or foam for easy access near the insertion zone for the catheter.

Figures 9, 10:
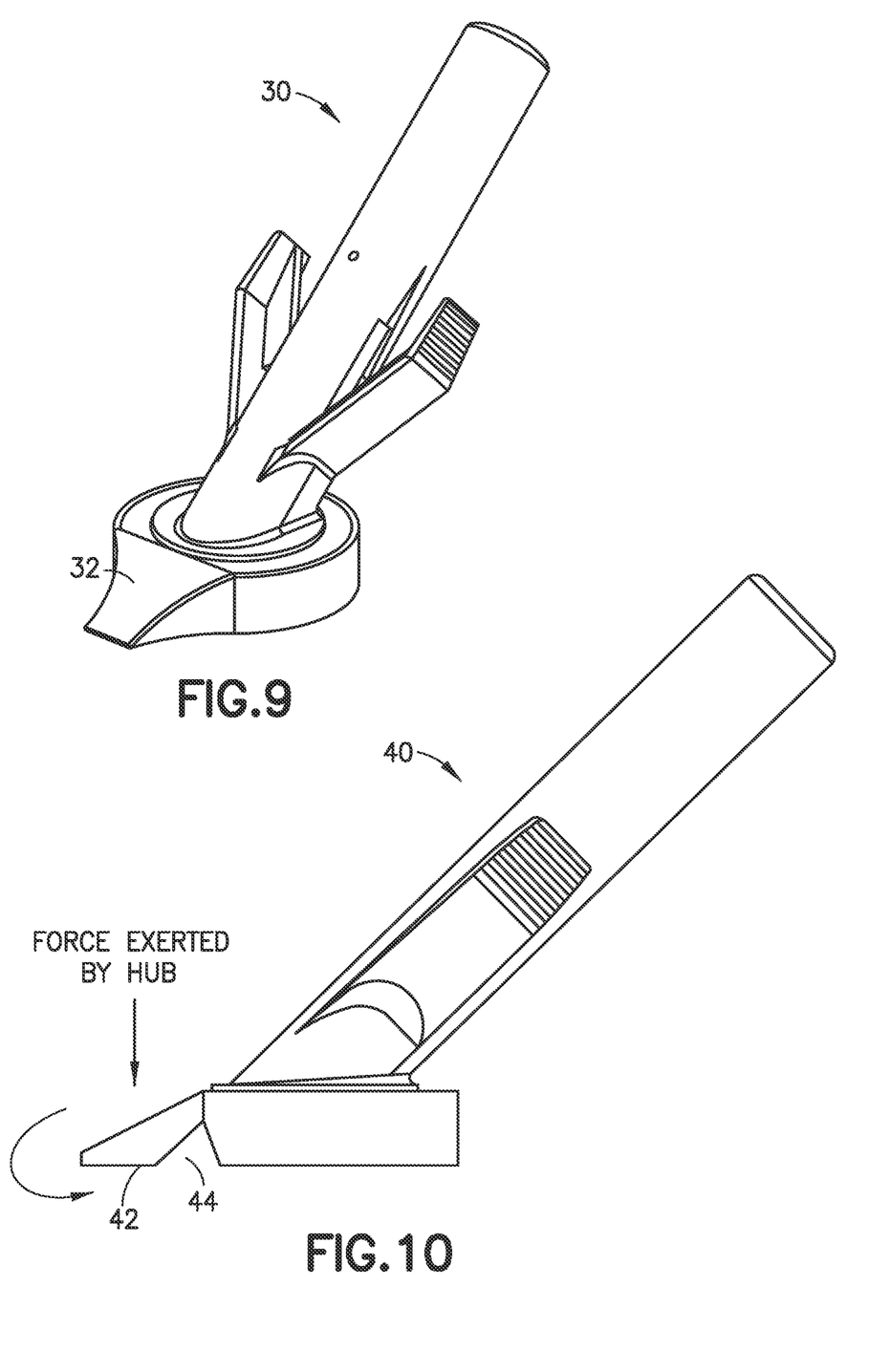
FIG. 9 is a perspective view of a skin preparation device according to another non-limiting embodiment or aspect of the present disclosure.
FIG. 10 is a side view of a skin preparation device according to another non-limiting embodiment or aspect of the present disclosure.

With reference to FIG. 9, according to one non-limiting embodiment or aspect of the present disclosure, a skin preparation device 30 may not include the slot or channel 12 of the skin preparation device 2 described above. In particular, instead of defining a slot or channel 12 in the tip 10 of the fluid retention member 8, the tip 32 of the skin preparation device 30 may taper in a downward direction and a radially inward direction to create a sharp nosed frontal tip similar to a knife edge made of sponge for easy access near the insertion zone for the catheter.

Figure 11:
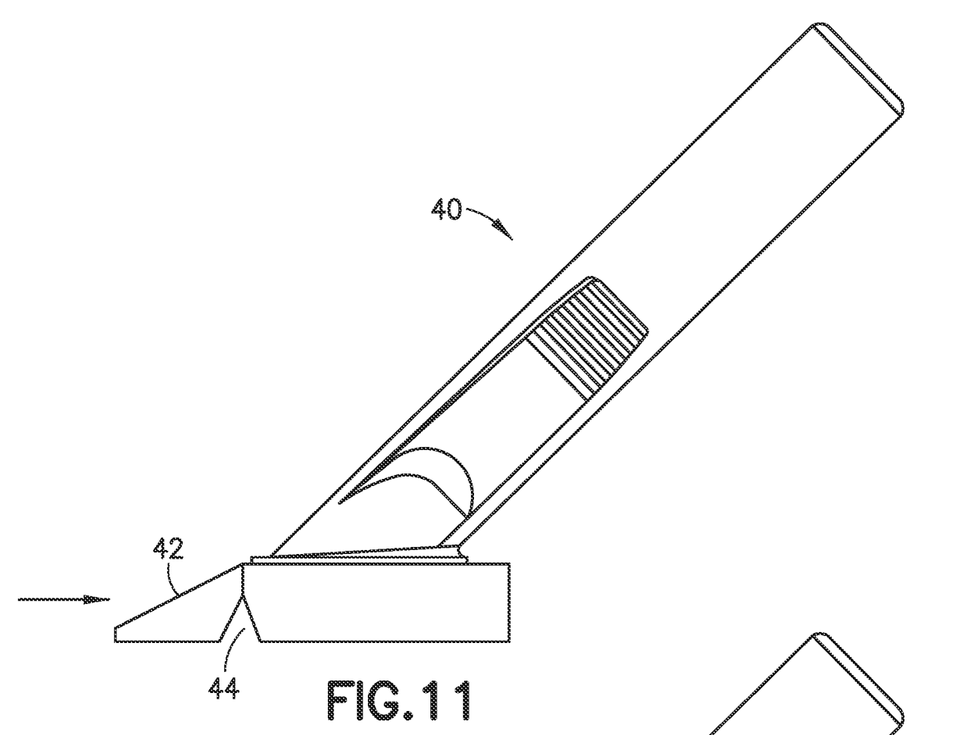
FIG. 11 is a side view of the skin preparation device of FIG. 10.
Figure 12:
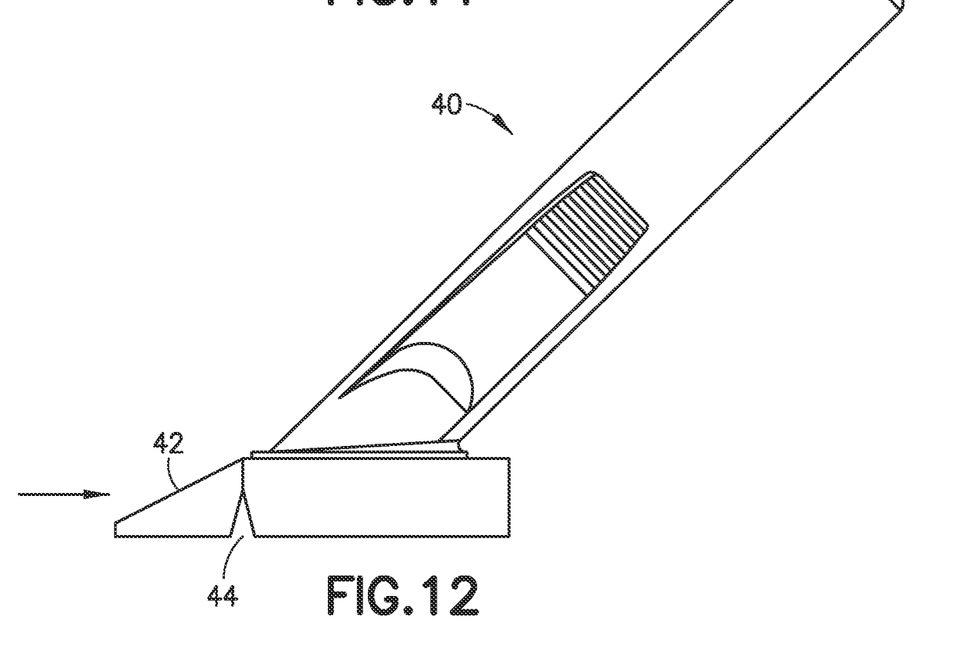
FIG. 12 is a side view of the skin preparation device of FIG. 10.

With reference to FIGS. 10-12, according to one non-limiting embodiment or aspect of the present disclosure, a skin preparation device 40 may include a tip 42 that is configured to deflect inwardly to modify angle A. The tip 42 of the skin preparation device 40 may define a cut-out 44 on the bottom surface of the tip 42. The cut-out 44 creates a living hinge about which the tip 42 of the skin preparation device 40 may rotate to adjust angle A. As shown in FIG. 10, as the tip 42 of the skin preparation device 40 is pushed towards the catheter hub, the tip 42 is able to rotate or deflect inwardly about the living hinge to move towards the cut-out 44. With reference to FIGS. 11 and 12, as the tip 42 is deflected further inward, angle A is reduced, thereby adjusting the tip 42 so as not to dislodge the catheter hub or catheter line. The variable angle design of the tip 42 aids in effective cleaning of the catheter connectors and tubes which are stabilized and secured with the patient. When the connector or tubes are already stabilized with the patient, the variable tip angle automatically adjusts based on the available space near the site of insertion 18. The variable tip angle provides an improvement for cleaning and disinfecting areas near a site of insertion 18, such as the patient's neck or chest, where the site of insertion 18 is challenging or difficult to reach.

The skin preparation devices 2, 20, 30, 40 described above provide a user with skin preparation for a patient before catheterization and provide catheter care with the advantage of cleaning and disinfecting the underside of a catheter hub, a catheter line, an IV line, and a site of insertion. In the skin preparation device 2 described above, the slot or channel 12 acts as a guide for travel of the skin preparation device 2 underneath the catheter hub, which unexpectedly disinfects the catheter hub as a result.

While embodiments of a skin preparation device are shown in the accompanying figures and described hereinabove in detail, other embodiments will be apparent to, and readily made by, those skilled in the art without departing from the scope and spirit of the invention. Accordingly, the foregoing description is intended to be illustrative rather than restrictive. The invention described hereinabove is defined by the appended claims and all changes to the invention that fall within the meaning and the range of equivalency of the claims are to be embraced within their scope.

The invention claimed is:

1. A skin preparation device, comprising:
   a body member;
   a fluid retention member operatively connected to a distal end of the body member; and
   a tip extending radially from an outer surface of the fluid retention member;
   further comprising at least one activation member extending radially from the body member, in which the at least one activation member is configured to release disinfectant held in the body member to the fluid retention member.

2. The skin preparation device of claim 1, wherein the body member is tubular and defines a hollow cavity to receive a disinfectant within the hollow cavity.

3. The skin preparation device of claim 1, wherein the fluid retention member comprises a sponge or foam.

4. The skin preparation device of claim 1, further comprising a base member formed on the distal end of the body member, in which the fluid retention member is operatively connected to the base member.

5. The skin preparation device of claim 1, wherein the tip defines a slot or channel.

6. The skin preparation device of claim 5, wherein an angle established between the slot or channel and a horizontal surface on which the skin preparation device rests is 165 degrees at a maximum.

7. The skin preparation device of claim 1, wherein the fluid retention member is replaceable on the body member.

8. The skin preparation device of claim 1, wherein the tip is tapered from an upper surface to a bottom surface.

9. The skin preparation device of claim 8, wherein the tip tapers at a maximum angle of 15 degrees relative to a horizontal surface on which the fluid retention member rests.

10. The skin preparation device of claim 1, wherein a diameter of the tip is less than a diameter of the fluid retention member.

11. The skin preparation device of claim 1, wherein an angle that defines the tip extending from the fluid retention member is a minimum of 115 degrees.

12. A skin preparation device, comprising:
    a body member;
    a fluid retention member operatively connected to a distal end of the body member; and
    a tip extending radially from an outer surface of the fluid retention member, in which the tip is operatively connected to the fluid retention member by a living hinge.

13. The skin preparation device of claim 12, further comprising a cut-out defined between the tip and the fluid retention member.

14. The skin preparation device of claim 12, wherein the tip is configured to move about the living hinge towards the fluid retention member upon a force being applied to an upper surface of the tip.

15. The skin preparation device of claim 12, wherein the fluid retention member and the tip are made of a sponge or foam.

16. The skin preparation device of claim 12, wherein the tip defines a slot or channel.

17. The skin preparation device of claim 12, wherein an outer diameter of the tip is less than an outer diameter of the fluid retention member.

18. A method of cleaning or disinfecting a catheter hub or catheter line, the method comprising:
    positioning a fluid retention member of a skin preparation device against a skin surface of a patient, in which the fluid retention member comprises a tip defining a slot or channel; and
    moving the fluid retention member in a sideways rotational movement about the catheter hub or catheter line.

19. The method of claim 18, wherein the tip of the fluid retention member is configured to deflect upon a force being applied to an upper surface of the tip.

20. A skin preparation device, comprising:
    a body member;
    a fluid retention member operatively connected to a distal end of the body member; and
    a tip extending radially from an outer surface of the fluid retention member;
    wherein the tip is tapered from an upper surface to a bottom surface.

* * * * *